United States Patent [19]
Weinberger

[11] Patent Number: 5,814,462
[45] Date of Patent: Sep. 29, 1998

[54] BIOCHEMICAL MARKERS OF ISCHEMIA

[75] Inventor: Judah Weinberger, Teaneck, N.J.

[73] Assignee: The Trustees of Columbia University in the City of New York, New York, N.Y.

[21] Appl. No.: 724,794

[22] Filed: Oct. 2, 1996

Related U.S. Application Data

[60] Provisional application No. 60/004,657 Oct. 2, 1995.

[51] Int. Cl.$^6$ ............................ G01N 33/53; A61K 35/14
[52] U.S. Cl. ........................... 435/7.1; 436/811; 436/815; 530/380; 530/399
[58] Field of Search .............................. 435/7.1; 436/811; 436/815; 530/380, 399

[56] References Cited

U.S. PATENT DOCUMENTS 5,306,724   4/1994   Goldberg ................................ 514/369

OTHER PUBLICATIONS

Aiello, L.P., Avery, R., Arrigg, P.G., Keyt, B.A., Jampel, H.D., Shah, S.T., Pasquale, L.R., Thieme, H., Iwamoto, M.A., Park, J.E., Nguyen, H.V., Aiello, L.M., Ferrara, N., and King, G.L., (Dec., 1994). "Vascular Endothelial Growth Factor in Ocular Fluid of Patients with Diabetic Retinopathy and Other Retinal Disorders", The New England of Medicine, 33: 1480–1487 (Exhibit 2).

Banai, S., Shweiki, D., Pinson A., Chandra, M., Lazarovici, G., and Keshet, E., (Aug., 1994). "Upregulation of Vascular Endothelial Growth Factor Expression Induced by Myocardial Ischaemia: Implications For Coronary Angiogenesis", Cardiovascular Research, 28: 1176–1179.

Blood, V.F., Magno, M.C., Bailey, W.F., Shi, Y., Yurgenev, L., DiMeo, F., Edie, R.N., and Mannion, J.D., (Nov., 1994). "Basic Fibroblast Growth Factor Identified in Chronically Stimulated Cardiomyoplasties" The Annals of Thoracic Surgery, 58: 1320–1326.

Clarke, M.S.F., Caldwell, R.W., Chiao, H., Miyake, K., and McNeil, P.L., (Jun., 1995). "Contraction–Induced Cell Wounding and Release of Fibroblast Growth Factor in Heart", Circulation Research, 76: 927–934.

Endoh, M., Pulsinelli, W.A., and Wagner, J.A., (Mar., 1994). "Transient Global Ischemia Induces Dynamic Changes in the Expression of bFGF and the FGF Receptor", Molecular Brain Research, 22: 76–88.

Shmuel Bania et al. Upreulation of Vascular Endothelial Growth Factor Expression Induced by Myocardial Ischaemia: Implications for Coronary Angiogenesis. Cardiovascular Research, 1994; 28: pp. 1176–1179.

M.B. Zimmering et al. Increased Basic Fibroblast Growth Factor in Plasma from Multiple Endocrine Neoplasia Type 1; Relation to Pituitary Tumor. Journal of Clinical Endocrinology and Metabolism, 1993; vol. 76. No. 5, pp. 1182–1187.

Kiyohide Fujimoto et al. Increased Serum Levels of Basic Fibroblast Growth Factor in Patients with Renal Cell Carcinoma. Biochemical and Biophysical Research Communication, Oct. 15, 1991; vol. 180. No. 1, pp. 386–392.

Wolfgang Schaper, et al. Molecular Biologic Concepts of Coronary Anastomoses. American College of Cardiology, Mar. 1, 1990; vol. 15. No. 3, pp. 513–518.

Neil J. Weissman, et al. Effect of β–Adrenergic Receptor Blockage on the Physiologic Response to Dobutamine Stress Echocardiography. American Heart Journal, 1995; vol. 130, No. 2, pp. 248–253.

Hashimoto, E., Ogita, T., Nakaoka, T., Matsuoka, R., Takao, A., and Kira, Y., (Nov., 1994). "Rapid Induction of Vascular Endothelial Growth Factor Expression by Transient Ischaemia in Rat Heart", American Journal of Physiology, 36: H1948–H1954.

Kiyota, Y., Takami, K., Iwane, M., Shino, A., Miyamoto, M., Tsukuda, R., and Nagaoka, A., (1991). "Increase in Basic Fibroblast Growth Factor–Like Immonoreactivity in Rat Brain After Forebrain Ischemia", Brain Research, 545: 322–328.

Kumon, Y., Sakaki, S., Kadota, O., Matsuda, S., Fujita, H., Yoshimura H., and Sakanaka, M., (1993). "Transient Increase in Endogenous Basic Fibroblast Growth Factor in Neurons of Ischemic Rat Brains", Brain Research, 605: 169–174.

Lippoldt, A., Andbjer, B., Rosen, L., Richter, E., Ganten, D., Cao, Y., Pettersson, R.F., and Fuxe, K., (1993). "Photochemically Induced Focal Cerebral Ischemia in Rat: Time Dependent and Global Increase in Expression of Basic Fibtoblast Growth Factor mRNA", Brain Research, 625: 45–56.

Nilsson, J., Elgue, G., Wallin M., Hamsten, A., and Blomback, M., (1989). "Correlation Between Plasma Levels of Growth Factors and Von willebrand Factor", Thrombosis Research, 54: 125–132.

Rabbath, P. Boochard, M., Martel., R., Fleser, A., Voisine, P., and Leclerc, G., (Oct., 1994). "Circulating Levels of Basic Fibroblast Growth Factor in Patients Undergoing PTCA", Circulation, 90(4), part 2, Abstract No. 1643, p. I–305.

(List continued on next page.)

*Primary Examiner*—James C. Housel
*Assistant Examiner*—Rodney P. Swartz
*Attorney, Agent, or Firm*—John P. White; Peter J. Phillips; Cooper & Dunham LLP

[57]  ABSTRACT

A method for identifying the presence of spontaneous ischemia in a subject comprised of obtaining biological samples from the subject at each of a plurality of time intervals within 18 hours of the onset of a symptom, measuring the amount of an angiogenic growth factor in the biological samples at each of the plurality of time intervals, and comparing the amounts of the angiogenic growth factor measured, wherein decreasing amounts of the angiogenic growth factor during the time intervals is indicative of spontaneous ischemia. Methods for identifying the presence of ischemia induced by an exercise or a pharmaceutical composition in a subject are also described.

34 Claims, 1 Drawing Sheet

OTHER PUBLICATIONS

Schaper, W., (1991). "Angiogenesis in The Adult Heart", Supplement to Basic Research in Cardiology, Suppl. 2, 86: 51–56.

Schneider, M.D., Robb McLellan, W., Black, F.M., and Parker, T.G., (1992). "Growth Factors, Growth Factors Response Elements, and The Cardiac Phenotype", Supplement to basic Research in Cardiology, Suppl. 2, 87: 33–48.

Takami, K., Iwane, M., Kiyota, Y., Miyamoto, M., Tsukuda, R., and Shiosaka, D., (1992). "Increase in Basic Fibroblast Growth Factor Immunoreactivity and its mRNA Level in Rat Brain Following Transient Forebrain Ischemia", Experimental Brain Research, 90: 1–10.

Takami, K., Kiyota, Y., Iwane, M., Miyamoto, M., Tsukuda, R., Igarashi, K., Shino., A., Wanaka, A., Shiosaka, S., and Tohyama, M., (1993). "Upregulation of Fibroblast Growth factor–receptor messenger RNA Expression in Rat Brain Following Transient Forebrain Ischemia", Experimental Brain Research, 97: 185–194.

Stedman's Medical Dictionary, 26th Edition, 1995 Williams & Wilkins, Baltimore, MD. p. 894.

BIOCHEMICAL MARKERS OF ISCHEMIA

This application claims the benefit of U.S. Provisional Application No. 60/004,657, filed October 2, 1995.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

The diagnosis of acute myocardial infarction is facilitated by clinically available assays for creatine phosphokinase isoenzymes, and more recently for troponin- t which may also be useful in identifying subjects with unstable angina and threatened infarction (1). Presently, no such biochemical markers are readily available for the diagnosis of myocardial ischemia in subjects with stable angina. The availability of such a marker could complement currently used clinical, electrocardiographic and exercise imaging techniques in diagnosing equivocal cases and could potentially obviate the need for more expensive testing in less equivocal presentations.

Local biochemical alterations in response to tissue ischemia or hypoxia include synthesis and secretion of mitogenic growth factors such as vascular endothelial growth factor (VEGF), beta-endothelial cell growth factor and acidic and basic fibroblast growth factor (bFGF) (2,3). These angiogenic proteins promote the proliferation of vascular smooth muscle cells and formation of new blood vessels (4).

Basic fibroblast growth factor, the most extensively studied of these polypeptides, is an 18–24 kd member of a family of heparin-binding polypeptides. It is widely distributed throughout the body, being found in many human neuroectodermal and mesodermal tissues, including the heart (5). Its expression is enhanced in animal models of cerebral (6,7) and in skeletal muscle ischemia (8) as well as in myocardial ischemia (9,10). It has recently been demonstrated that intracoronary administration of bFGF promotes angiogenesis and collateral formation in areas of ischemic and infarcted porcine and canine hearts (11–14).

Enzyme linked immunoassays (ELISA) are available for detection of bFGF and VEGF in human serum, and bFGF levels have been shown to be elevated in subjects with a variety of tumors (15–17). Urine assays for bFGF have been shown to be useful for the detection of human renal cell carcinomas (18). With the recent development of a more sensitive urine ELISA (detection limit of 0.1 pg/ml), baseline levels of bFGF and VEGF can be accurately quantitated in healthy controls, and elevated levels have been shown to correlate with the presence of multiple solid tumors, lymphoma and leukemia (19).

Therefore, given their demonstrated enhanced expression and angiogenic role in animal models of myocardial ischemia and the feasibility of sensitive urine quantitation in humans, the usefulness of bFGF and VEGF as biochemical markers of exercise induced ischemia are addressed by the present invention.

SUMMARY OF THE INVENTION

The present invention provides a method for identifying the presence of spontaneous ischemia in a subject which comprises:

(a) obtaining biological samples from the subject at each of a plurality of time intervals within 18 hours of the onset of a symptom;

(b) measuring the amount of an angiogenic growth factor in the biological samples at each of the plurality of time intervals; and (c) comparing the amounts of the angiogenic growth factor measured in step (b), wherein decreasing amounts of the angiogenic growth factor during the time intervals is indicative of spontaneous ischemia.

The present invention further provides methods for identifying the presence of ischemia induced by an exercise or a pharmaceutical composition in a subject.

DETAILED DESCRIPTION OF THE INVENTION

Figure 1:
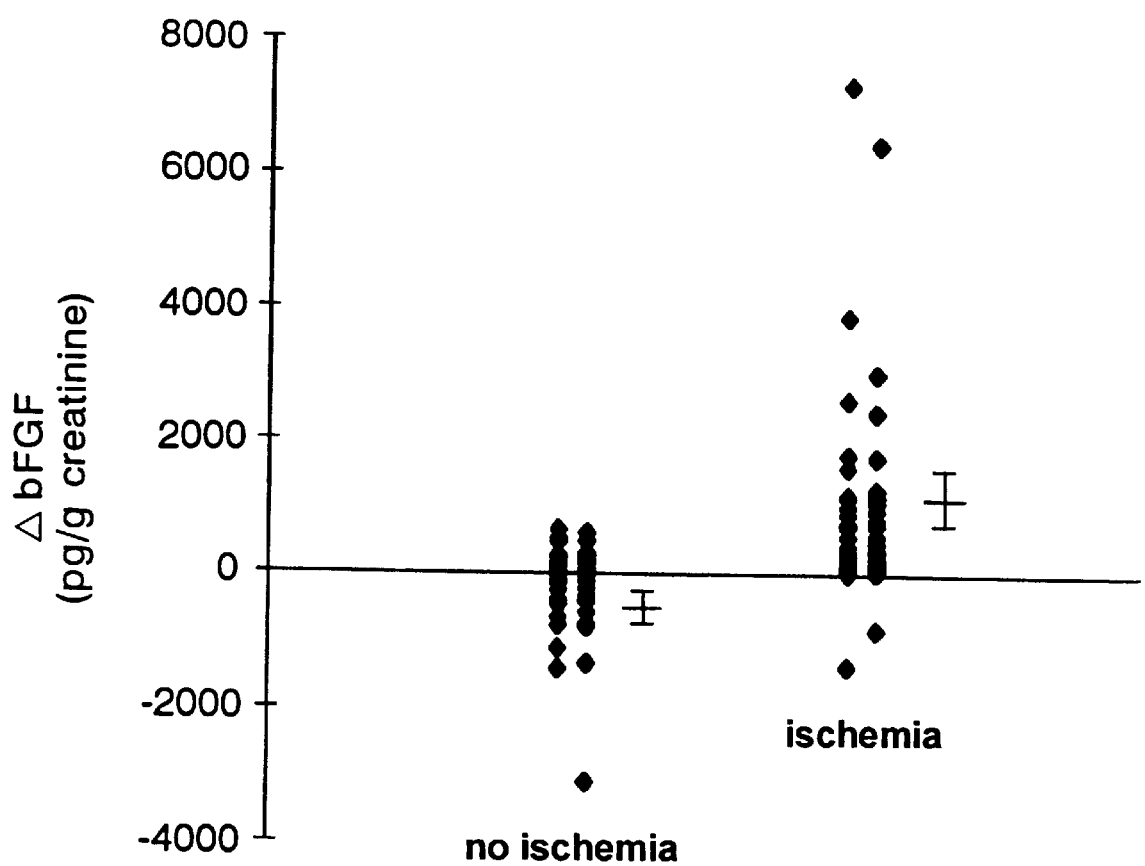
FIG. 1 shows a scatter plot of the change in normalized bFGF amounts (pg bFGF/g creatinine) in urine comparing amounts prior to exercise to amounts measured 3 hours after exercise testing. Subjects are identified as ischemic if a reversible thallium defect or electrocardiogram (ECG) criteria for ischemia are detected. The mean change in urine bFGF in response to exercise was $-277\pm130$ pg bFGF/g creatinine for subjects without ischemia and $1052\pm245$ pg bFGF/g creatinine for those with ischemia ($p<0.0001$).

The present invention provides a method for identifying the presence of spontaneous ischemia in a subject which comprises:

(a) obtaining biological samples from the subject at each of a plurality of time intervals within 18 hours of the onset of a symptom;

(b) measuring the amount of an angiogenic growth factor in the biological samples at each of the plurality of time intervals; and (c) comparing the amounts of the angiogenic growth factor measured in step (b), wherein decreasing amounts of the angiogenic growth factor during the time intervals is indicative of spontaneous ischemia.

In one embodiment of the invention, the spontaneous ischemia is cardiac ischemia and the symptom is chest pain, shortness of breath, dizziness, or a combination thereof.

In another embodiment of the invention, the subject is a mammal such as a human.

In yet another embodiment of the invention, the biological sample is selected from the group consisting of urine, blood, serum, joint fluid, and cerebrospinal fluid.

In another embodiment of the invention, the angiogenic growth factor is vascular endothelial growth factor (VEGF) or a fibroblast growth factor such as basic fibroblast growth factor (bFGF).

In yet another embodiment of the invention, the amount of the angiogenic growth factor can be determined using any of the following non-limiting assays: radioimmunoassay (RIA); enzyme-linked immunosorbent assay (ELISA); specific protein mass assay; or activity assay.

In another embodiment of the invention the amount of the angiogenic growth factor is determined from the biological sample(s) taken after the onset of the symptom and is compared to a standard amount of angiogenic growth factor calculated from a control population, wherein an elevated amount of the angiogenic growth factor in the biological sample(s) is indicative of ischemia. This is particularly useful in ischemic states which result in a more sustained increase in angiogenic growth factor amounts. For example, chronic lower extremity ischemia or ischemia of an abdominal viscus can be ongoing for days, and thus a sustained release or increase of growth factor amounts may occur. Detection of increased amounts of angiogenic growth factors over standard amounts calculated from a control population would be indicative of ishemia.

The present invention further provides a method for identifying the presence of ischemia induced by an exercise in a subject which comprises:

(a) obtaining a biological sample from the subject prior to the exercise;

(b) obtaining a second biological sample from the subject following completion of the exercise;

(c) measuring the amounts of an angiogenic growth factor in the biological samples obtained in steps (a) and (b); and (d) comparing the amounts of the angiogenic growth factor measured in step (c), wherein an elevated amount of the angiogenic growth factor in the biological sample obtained in step (b) is indicative of ischemia.

In one embodiment of the invention, the ischemia is cardiac ischemia.

In another embodiment of the invention, the subject is a mammal such as a human.

In yet another embodiment of the invention, the biological sample is selected from the group consisting of urine, blood, serum, joint fluid, and cerebrospinal fluid.

In another embodiment of the invention, the angiogenic growth factor is vascular endothelial growth factor (VEGF) or a fibroblast growth factor such as basic fibroblast growth factor (bFGF).

In yet another embodiment of the invention, the amount of the angiogenic growth factor can be determined using any of the following non-limiting assays: radioimmunoassay (RIA); enzyme-linked immunosorbent assay (ELISA); specific protein mass assay; or activity assay.

In another embodiment of the invention the amount of the angiogenic growth factor is determined from the biological sample(s) taken after the exercise and is compared to a standard amount of angiogenic growth factor calculated from a control population, wherein an elevated amount of the angiogenic growth factor in the biological sample(s) is indicative of ischemia.

The present invention also provides a method for identifying the presence of ischemia induced by a pharmaceutical composition in a subject which comprises:

(a) obtaining a biological sample from the subject prior to administration of the pharmaceutical composition;

(b) obtaining a second biological sample from the subject following administration of the pharmaceutical composition;

(c) measuring the amounts of an angiogenic growth factor in the biological samples obtained in steps (a) and (b); and (d) comparing the amounts of the angiogenic growth factor measured in step (c), wherein an elevated amount of the angiogenic growth factor in the biological sample obtained in step (b) is indicative of ischemia.

In one embodiment of the invention, the ischemia is cardiac ischemia.

In another embodiment of the invention, the pharmaceutical composition comprises an active ingredient and a pharmaceutically acceptable carrier. In one preferred embodiment the active ingredient is dobutamine.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The active ingredient can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The active ingredient can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular active ingredient in use, the strength of the preparation, the mode of administration, and the advancement of the disease condition. Additional factors depending on the particular subject being evaluated will result in a need to adjust dosages, including subject age, weight, gender, diet, and time of administration.

In another embodiment of the invention, the subject is a mammal such as a human.

In yet another embodiment of the invention, the biological sample is selected from the group consisting of urine, blood, serum, joint fluid, and cerebrospinal fluid.

In another embodiment of the invention, the angiogenic growth factor is vascular endothelial growth factor (VEGF) or a fibroblast growth factor such as basic fibroblast growth factor (bFGF).

In yet another embodiment of the invention, the amount of the angiogenic growth factor can be determined using any of the following non-limiting assays: radioimmunoassay (RIA); enzyme-linked immunosorbent assay (ELISA); specific protein mass assay; or activity assay.

In another embodiment of the invention the amount of the angiogenic growth factor is determined from the biological sample(s) taken after administration of the pharmaceutical composition and is compared to a standard amount of angiogenic growth factor calculated from a control population, wherein an elevated amount of the angiogenic growth factor in the biological sample(s) is indicative of ischemia.

The levels of bFGF and VEGF can be accurately measured in urine and are significantly increased in subjects with exercise induced ischemia. A circulating biochemical marker of ischemia has not previously been identified in mammals i.e. humans. Ribbach et al. briefly reported an increase in circulating serum levels of bFGF in subjects undergoing coronary angioplasty as compared to subjects undergoing only catheterization (22). However, factors other than balloon occlusion ischemia likely contributed to this observation. Endothelial injury as is produced by balloon dilatation may induce synthesis and release of bFGF (23, 24), though this has not been consistently found (25). In addition, heparin, which is routinely administered during coronary angioplasty, is known to release FGF-like activity into the circulation, possibly by FGF displacement from its extracellular matrix (26). No subjects reported herein had received heparin, and the effect of endothelial injury (venipuncture) would be minimized by the presence of a control (non-ischemic) population.

Clinical and demographic characteristics did not significantly affect baseline bFGF levels and magnitude of change was not related to baseline level. There was a trend toward higher baseline levels in females (2040 vs. 1489 pg bFGF/g creatinine, p=0.1) which has been previously observed (18). Males had a non-significantly greater increase (584 vs 85 pg bFGF/g creatinine, p=0.08) after exercise which may be related to a greater myocardial mass and hence quantitatively more ischemia. When analyzed separately, however, both males (p<0.0001) and females (p<0.05) had significant increases in bFGF when ischemic.

If myocardial mass is a determinant, a history of hypertension might be expected to be associated with a greater bFGF response. However, this was not found to be the case. The effect of anti-hypertensive medications (which may also be anti-ischemic) was not assessed, but may contribute to this observation, as adrenergic blockade and angiotensin inhibition may inhibit bFGF induction (27). Other factors likely contribute, since the presence of hypertrophy by electrocardiogram (ECG) voltage criteria was unrelated (though the number of observations was small, n=9) and the effect of hypertension was no longer significant on multivariate analysis.

Ischemia in the distribution of the right or left circumflex coronary was associated with a greater increase in bFGF than ischemia in the left anterior descending distribution. While this observation might be unexpected given the respective amounts of myocardium normally supplied by these arteries, the amount of viable myocardium subject to ischemia in this group of subjects may have been smaller in the subgroup demonstrating left anterior descending ischemia as this subgroup had a predominance of associated fixed defects by thallium scan (57% vs 18%).

Basic fibroblast growth factor and vascular endothelial growth factor, both angiogenic peptides induced by ischemia and integral in the development of coronary collaterals, can be accurately measured in human urine. Applicant has demonstrated that exercise induced ischemia assessed electrocardiographically and by thallium scintography is associated with a significant increase in urine excretion of bFGF and VEGF, and this effect is independent of clinical, demographic and exercise-related variables.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Over a four month period, 86 subjects (52 men, 34 women; mean [±SD] age 60±10 years) were referred to an exercise lab for evaluation of chest pain by exercise thallium study. Subjects were excluded from analysis if they gave a history of malignancy, peripheral vascular disease clinically (claudication) or by prior evaluation, coagulation disorders (including recent deep vein thrombosis or pulmonary embolus) or inability to exercise. Subjects were classified into two groups based on the presence or absence of ischemia by either ECG or scan criteria.

EXERCISE THALLIUM TEST

Symptom limited exercise testing was performed on a treadmill using a standard Bruce Protocol (20). Termination of exercise was at the discretion of the physician performing the test based on symptoms of the subject, ECG, or the attaining of at least 85% of maximal predicted heart rate. 3 mCi of thallium-201 was injected approximately 40 seconds prior to termination of exercise. Planar scans and SPECT imaging were performed after recovery and redistribution scans were done at 4 hours. ECGs were analyzed for ischemic criteria and scans were evaluated for presence and distribution of fixed and reversible perfusion defects.

URINE bFGF AND VEGF ANALYSIS

A baseline urine specimen was obtained just prior to exercise and a post exercise specimen was obtained between 2 and 4 hours following exercise, prior to redistribution scanning. Levels of bFGF and VEGF (pg/ml) in samples prepared from the urine were measured using an enzyme/ELISA bioassay which uses recombinant human antibodies raised against recombinant bFGF or VEGF (21). The detection limit of the immunoassay is 0.1 pg/ml. Urine creatinine levels (g/ml) were determined (Sigma Diagnostics, St. Louis, Mont.). The levels of bFGF and VEGF were corrected for variation in urine creatinine excretion and expressed as pg/g creatinine.

STATISTICAL ANALYSIS

Results are expressed as mean values±SEM. Statistical significance was defined as a two-tailed p<0.05. Unpaired student t test was used to compare continuous variables between two groups. Single factor analysis of variance was used to compare continuous variables among multiple groups. Linear regression was performed to assess for relationships between two continuous variables, and multivariate analysis (backward stepwise multiple logistic regression) was performed to assess for independent relationships.

EXERCISE THALIUM

Forty-three (50%) subjects had ischemia by either ECG criteria or thallium scan. Twenty eight (33%) had ischemia by ECG and 29 (34%) had ischemia by scan. Perfusion defects were present in the right coronary and/or circumflex artery distribution in 22 (76%) subjects and to the anterior descending artery distribution in 7 ( 24%) subjects with ischemia. Fixed perfusion defects were present on 18 (21%) scans, 11 (61%) in the right coronary or circumflex and 7 (39%) in the anterior descending artery distribution. Fifteen (17%) subjects experienced chest pain during exercise. By univariate analysis the presence of ischemia was strongly associated with an increase in urine bFGF (FIG. 1). The mean change in urine bFGF in response to exercise was −277±130 pg bFGF/g creatinine for subjects without ischemia and 1052±245 pg bFGF/g creatinine for those with ischemia (p<0.0001) (Table 1). This association remained significant when using ECG (p<0.01) and scan (p=0.001) criteria for ischemia separately. There was no relationship between other exercise variables (heart rate-blood pressure product, Bruce stage achieved or occurrence of chest pain) and change in bFGF. Ischemia in a right and/or circumflex coronary artery distribution was associated with a greater increase in bFGF than ischemia in a left anterior descending artery distribution (1498±441 vs 432±144 pg bFGF/g creatinine, p<0.05). Scans with fixed defects were associated with a smaller increase in bFGF (93±234 vs 465±186 pg bFGF/g creatinine, p=0.01) but this did not achieve statistical significance.

TABLE 1

Exercise Induced Change in Urine bFGF. The amounts of bFGF are expressed in pg bFGF/g of creatinine.

|  | bFGF (pg/g) baseline | bFGF (pg/g) post-exercise | Δ bFGF (pg/g) | p Value |
|---|---|---|---|---|
| No Ischemia | 1812 ± 236 | 1535 ± 214 | −277 ± 130 | <0.0001 |
| Ischemia* | 1601 ± 268 | 2653 ± 412 | 1052 ± 245 | |

Values are expressed as mean ± SEM
*by ECG or Scan criteria

BASELINE CLINICAL VARIABLES

Subject demographics and clinical characteristics are represented in Table 2. By univariate analysis there was a negative association between hypertension and exercise induced urine bFGF response (67±166 vs 810±275 pg bFGF/g creatinine, p<0.05) There was no relationship between bFGF response and any other demographic or clinical variable. There was a trend toward a greater bFGF increase in men (584±233 vs 85±157 pg bFGF/g creatinine, p=0.08).

TABLE 2

Exercise Induced Change in Urine bFGF: Clinical Variables. The amounts of bFGF are expressed in pg bFGF/g of creatinine.

|  | n | Δ bFGF[1] + (pg/g) | Δ bFGF[2] − (pg/g) | p Value |
|---|---|---|---|---|
| Hypertension | 49 (57%) | 67 ± 166 | 810 ± 275 | <0.05 |
| Neurovascular Event | 7 (8%) | 660 ± 235 | 363 ± 168 | NS[3] |
| Congestive heart failure | 6 (7%) | −73 ± 501 | 421 ± 163 | NS |
| Prior CABG or PTCA | 21 (24%) | 548 ± 210 | 334 ± 195 | NS |
| Hyperlipidemia | 14 (16%) | 560 ± 675 | 353 ± 135 | NS |
| Diabetes Mellitis | 11 (13%) | 268 ± 292 | 404 ± 174 | NS |
| Myocardial Infarction | 29 (34%) | 506 ± 191 | 327 ± 215 | NS |
| Gender (male) | 52 (60%) | 584 ± 233 | 85 ± 157 | 0.08 |
| Age | — | — | — | NS |

Values are expressed as mean ± SEM
[1] the change in bFGF values for subjects with the indicated demographic or clinical characteristic
[2] the change in bFGF values for subjects without the indicated demographic or clinical characteristic
[3] not significant

VEGF LEVELS ARE ELEVATED IN CARDIAC ISCHEMIA

In a separate study, the levels of urinary VEGF were measured in four subjects prior to and following exercise (Table 3) as described in Experimental Procedures. A significant increase in the levels of VEGF was observed in every subject that was independently diagnosed (see Experimental Procedures) with cardiac ischemia. However, no increase in the level of VEGF was observed in the subject not suffering from cardiac ischemia.

TABLE 3

Exercise Induced Change in Urine VEGF. The amounts of bFGF are expressed in pg bFGF/g of creatinine.

| Ischemia | Chest Pain | VEGF (pg/g) before exercise | VEGF (pg/g) after exercise | Δ VEGF |
|---|---|---|---|---|
| yes | no | 11086 | 13205 | 2119 |
| yes | yes | 49672 | 886024 | 836352 |
| no | no | 65948 | 44084 | −21864 |
| yes | no | 19718 | 30849 | 11131 |

MULTIVARIATE ANALYSIS

In order to assess for independent predictors of ischemia, all exercise, demographic and clinical variables were entered into a stepwise multiple logistic regression analysis (SAS). Only bFGF and VEGF responses were independently related to exercise induced ischemia (p<0.001).

REFERENCES

1. Mair, J., Dienstl, F., Puschendorf, B. (1983) Cardiac troponin t in the diagnosis of myocardial injury. *Crit. Rev. Clin. Lab. Sci.* 29:31–57.

2. Levy, A. P., Levy, N. S., Loscalzo, J., et al. (1995) Regulation of vascular endothelial growth factor in cardiac myocytes. *Circ. Res.* 76:758–66.

3. Schaper, W., Sharma, H. S., Quinkler, W., et al. (1990) Molecular biologic concepts of coronary anastomoses. *J. Am. Coll. Cardiol.* 15:513–8.

4. Klagsbrun, M. (1991) Regulators of angiogenesis. *Ann. Rev. Physiol.* 53:217–39.

5. Ationu, A., Carter, N. (1994) Ventricular expression of basic fibroblast growth factor gene after orthotopic cardiac transplantation. *Transplantation* 57:1364–6.

6. Takami, K., Iwane, M., Kiyota, Y., et al. (1992) Increase of basic fibroblast growth factor immunoreactivity and its mRNA level in rat brain following transient forebrain ischemia. *Exp. Brain Res.* 90:1–10.

7. Endoh, M., Pulsinelli, W. A., Wagner, J. A. (1994) Transient global ischemia induces dynamic changes in the expression of bFGF and the FGF receptor. *Mol. Brain Res.* 22:76–88.

8. Chleboun, J. O., Martins, R. N. (1994) The development and enhancement of the collateral circulation in an animal model of lower limb ischemia. *Australian New Zealand J. Surg.* 64:202–7.

9. Cohen, M. V., Vernon, J., Yaghdjian, V., Hatcher, V. B. (1994) Longitudinal changes in myocardial basic fibroblast growth factor (FGF-2) activity following coronary artery ligation in the dog. *J. Mol. Cell Cardiol.* 26:683–90.

10. Hashimoto, E., Ogita, T., Nakaota, T., et al. Rapid (1990) induction of vascular endothelial growth factor expression by transient ischemia in the rat heart. *Am. J. Physiol.* 36:H1948–54.

11. Battler, A., Scheinowitz, M., Bor, A., et al. (1994) Intracoronary injection of basic fibroblast growth factor enhances angiogenesis in infarcted swine myocardium. *J. Am. Coll. Cardiol.* 22:2001–6

12. Unger, E. F., Banai, S., Shou, M., et al. (1994) Basic fibroblast growth factor enhances myocardial collateral flow in a canine model. *Am. J. Physiol.* 266:H1588–95.

13. Lazarous, D. F., Scheinowitz, M., Shou, M., et al. (1995) Effects of chronic administration of basic fibroblast growth factor on collateral development in the canine heart. *Circulation* 91:145–53.

14. Yanagisawa-Miwa, A., Uchida, Y., Nakamura, F., et al. (1992) Salvage of infarcted myocardium by angiogenic action of basic fibroblast growth factor. *Science* 257:1401–3.

15. Takei, Y., Higashira, H., Hayashi, K. (1995) Improvement of an EIA system of basic fibroblast growth factor by use of biotinylated antibody prepared with NHS-LC-biotin. *J. Clin. Lab. Anal.* 9:96–100.

16. Ii, M., Yoshida, H., Hada, T., et al. (1993) Improved enzyme immunoassay for human basic fibroblast growth factor using a new enhanced chemiluminescence system. *Biochem. Biophys. Res. Commun.* 193:540–5.

17. Zimering, M. B., Katsumata, N., Sato, Y., et al. (1993) Increased basic fibroblast growth factor in plasma from multiple endocrine neoplasia type 1: relation to pituitary tumor. *J. Clin. Endocrin. Metab.* 76:1182–7.

18. Fujimoto, K., Ichimora, Y., Kakizoe, T., et al. (1991) Increased levels of basic fibroblast growth factor in patients with renal cell carcinoma. *Biochem. Biophys. Res. Com.* 180:386–92.

19. Nguyen, M., Watanabe, H., Budsen, A. E., et al. (1994) Elevated levels of an angiogenic peptide, basic fibroblast growth factor, in the urine of patients with a wide spectrum of cancers. *J. Natl. Cancer Inst.* 86:356–61.

20. Ellestad, M. H. (1986) Stress Testing. Principles and Practice. 3rd ed. Philadelphia, FA Davis.

21. R&D Systems, Inc., Minneapolis, Minn. (1995) *Ouantikine ELISA Handbook.*

22. Ribach, P., Bouchard, M., Martel, R., et al. (1994) Circulating levels of basic fibroblast growth factor in patients undergoing PTCA (abstr.). *Circulation* 90:I-305.

23. Lindner, V., Lappi, D. A., Baird, A., Majack, R. A., Reidy, M. A. (1991) Role of basic fibroblast growth factor in vascular lesion formation. *Circ. Res.* 68:106–13.

24. Lindner, V., Reidy, M. A. (1991) Proliferation of smooth muscle cells after vascular injury is inhibited by an antibody against basic fibroblast growth factor. *Proc. Natl. Acad. Sci. USA* 88:3739–43.

25. Olsen, N. E., Chao, S., Lindner, V., Reidy, M. (1992) Intimal smooth muscle cell proliferation after balloon catheter injury: the role of basic fibroblast growth factor. *Am. J. Path.* 140:1017–23.

26. Unger, E. F., Banai, S., Shou, M., et al. (1993) A model to assess interventions to improve collateral blood flow: continuous administration of agents into the left coronary artery in dogs. *Cardiovasc. Res.* 27:785–91.

27. Dzau, V. J. (1994) Cell biology and genetics of angiotensin in cardiovascular disease. *J. Hypertension* 12:S3–10.

What is claimed is:

1. A method for identifying the presence of ischemia in a subject with a statistical baseline angiogenic growth factor level which comprises:

(a) obtaining biological samples from the subject at each of a plurality of time intervals within 18 hours of the onset of a symptom including at least one of a chest pain, shortness of breath, and dizziness;

(b) measuring the amount of an angiogenic growth factor in the biological samples at each of the plurality of time intervals; and (c) comparing the amounts of the angiogenic growth factor measured in step (b), wherein the presence of amounts of the angiogenic growth factor above the statistical baseline during the time intervals is indicative of the occurrence of ischemia at a time substantially contemporaneous with the onset of said symptom.

2. The method of claim 1, wherein the ischemia is cardiac ischemia.

3. The method of claim 1, wherein the symptom is a combination of chest pain, shortness of breath, and dizziness.

4. The method of claim 1, wherein the subject is a mammal.

5. The method of claim 4, wherein the mammal is a human.

6. The method of claim 1, wherein the biological sample is urine.

7. The method of claim 1, wherein the biological sample is selected from the group consisting of blood, serum, joint fluid, and cerebrospinal fluid.

8. The method of claim 1, wherein the angiogenic growth factor is a fibroblast growth factor.

9. The method of claim 8, wherein the fibroblast growth factor is basic fibroblast growth factor (bFGF).

10. The method of claim 1, wherein the angiogenic growth factor is vascular endothelial growth factor (VEGF).

11. The method of claim 1, wherein the amount of the angiogenic growth factor is determined by radioimmunoassay (RIA), enzyme-linked immunosorbent assay (ELISA), specific protein mass assay, or activity assay.

12. A method for identifying the presence of ischemia induced by an exercise in a subject which comprises:
(a) obtaining a biological sample from the subject prior to the exercise;
(b) obtaining a second biological sample from the subject following completion of the exercise;
(c) measuring the amounts of an angiogenic growth factor in the biological samples obtained in steps (a) and (b); and
(d) comparing the amounts of the angiogenic growth factor measured in step (c), wherein an elevated amount of the angiogenic growth factor in the biological sample obtained in step (b) is indicative of ischemia.

13. The method of claim 12, wherein the ischemia is cardiac ischemia.

14. The method of claim 12, wherein the subject is a mammal.

15. The method of claim 14, wherein the mammal is a human.

16. The method of claim 12, wherein the biological sample is urine.

17. The method of claim 12, wherein the biological sample is selected from the group consisting of blood, serum, joint fluid, and cerebrospinal fluid.

18. The method of claim 12, wherein the angiogenic growth factor is a fibroblast growth factor.

19. The method of claim 18, wherein the fibroblast growth factor is basic fibroblast growth factor (bFGF).

20. The method of claim 12, wherein the angiogenic growth factor is vascular endothelial growth factor (VEGF).

21. The method of claim 12, wherein the amount of the angiogenic growth factor is determined by radioimmunoassay (RIA), enzyme-linked immunosorbent assay (ELISA), specific protein mass assay, or activity assay.

22. A method for identifying the presence of ischemia induced by a pharmaceutical composition in a subject which comprises:
(a) obtaining a biological sample from the subject prior to administration of the pharmaceutical composition;
(b) obtaining a second biological sample from the subject following administration of the pharmaceutical composition;
(c) measuring the amounts of an angiogenic growth factor in the biological samples obtained in steps (a) and (b); and
(d) comparing the amounts of the angiogenic growth factor measured in step (c), wherein an elevated amount of the angiogenic growth factor in the biological sample obtained in step (b) is indicative of ischemia.

23. The method of claim 22, wherein the ischemia is cardiac ischemia.

24. The method of claim 22, wherein the pharmaceutical composition comprises an active ingredient and a pharmaceutically acceptable carrier.

25. The method of claim 24, wherein the active ingredient is dobutamine.

26. The method of claim 22, wherein the subject is a mammal.

27. The method of claim 26, wherein the mammal is a human.

28. The method of claim 22, wherein the biological sample is urine.

29. The method of claim 22, wherein the biological sample is selected from the group consisting of blood, serum, joint fluid, and cerebrospinal fluid.

30. The method of claim 22, wherein the angiogenic growth factor is a fibroblast growth factor.

31. The method of claim 30, wherein the fibroblast growth factor is basic fibroblast growth factor (bFGF).

32. The method of claim 22, wherein the angiogenic growth factor is vascular endothelial growth factor (VEGF).

33. The method of claim 22, wherein the amount of the angiogenic growth factor is determined by radioimmunoassay (RIA), enzyme-linked immunosorbent assay (ELISA), specific protein mass assay, or activity assay.

34. A method for identifying the presence of ischemia in a subject, which comprises:
(a) determining a baseline angiogenic growth factor level by taking a plurality of baseline-determining measurements of the angiogenic growth factor level of the subject over one of a first time interval before the occurance of ischemia and a second time interval beginning more than about 18 hours after the occurance of ischemia;
(b) obtaining biological sample potentially indicative of ischemia from the subject at each of a plurality of time intervals within 18 hours of the onset of a symptom including at least one of a chest pain, shortness of breath, and dizziness;
(c) measuring the amount of an angiogenic growth factor in the biological samples potentially indicative of ischemia at each of the plurality of time intervals; and
(d) comparing the amounts of the angiogenic growth factor measured in step (c), wherein the presence of amounts of the angiogenic growth factor above the baseline during the time intervals is indicative of the occurrence of ischemia at a time substantially contemporaneous with the onset of said symptom.

* * * * *